United States Patent [19]

Beyar et al.

[11] Patent Number: 5,372,600
[45] Date of Patent: Dec. 13, 1994

[54] STENT DELIVERY SYSTEMS

[75] Inventors: Mordechay Beyar, Tel-Aviv; Oren Globerman, Holon; Daniel Yachia, Herzliya-On-Sea, all of Israel

[73] Assignee: InStent Inc., Eden Prairie, Minn.

[21] Appl. No.: 60,397

[22] Filed: May 10, 1993

Related U.S. Application Data

[63] Continuation-in-part of Ser. No. 805,737, Dec. 11, 1991, abandoned, which is a continuation-in-part of Ser. No. 781,174, Oct. 31, 1991, abandoned.

[51] Int. Cl.$^5$ .............................................. A61B 17/00
[52] U.S. Cl. ................................. 606/108; 606/194
[58] Field of Search ............... 604/96; 606/108, 151, 606/191, 192, 194, 195, 198; 623/1, 12

[56] References Cited

U.S. PATENT DOCUMENTS

| | | |
|---|---|---|
| 2,499,045 | 2/1950 | Walker et al. . |
| 4,768,507 | 6/1988 | Fischell et al. . |
| 4,771,773 | 9/1988 | Kropf . |
| 4,795,458 | 1/1989 | Regan . |
| 4,878,906 | 7/1989 | Lindemann et al. . |
| 4,913,141 | 3/1990 | Hillstead . |
| 5,108,416 | 4/1992 | Ryan . |
| 5,147,370 | 9/1992 | McNamara et al. . |

FOREIGN PATENT DOCUMENTS 2020557 11/1979 United Kingdom .
830097 3/1883 WIPO .
9004982 5/1990 WIPO .

OTHER PUBLICATIONS

E. J. G. Milroy et al., "A New Treatment For Urethral Strictures": A Permanently Inplanted Urethral Stent Journal of Urology, vol. 141, May, 1989 pp. 1120–1122.

*Primary Examiner*—Edgar S. Burr
*Assistant Examiner*—Ren Yan
*Attorney, Agent, or Firm*—Cowan, Liebowitz & Latman

[57] ABSTRACT

This invention is directed to stent delivery systems. In one embodiment an apparatus for implanting a flexible, generally cylindrical, expandable stent, comprises a catheter having distal and proximal ends, the catheter defining a central lumen and a second lumen extending therethrough and having two longitudinally displaced openings extending from the second lumen radially to the surface of the catheter; a flexible, expandable stent having discrete proximal and distal ends, the stent being positioned circumferentially around the catheter and the discrete ends extending into the openings to hold the stent in position; and at least one release wire positioned in and extending through the second lumen, the release wire or wires fixedly containing at least one conically shaped pushing member capable of causing a discrete end of the stent to move radially as the release wire is moved proximally.

34 Claims, 7 Drawing Sheets

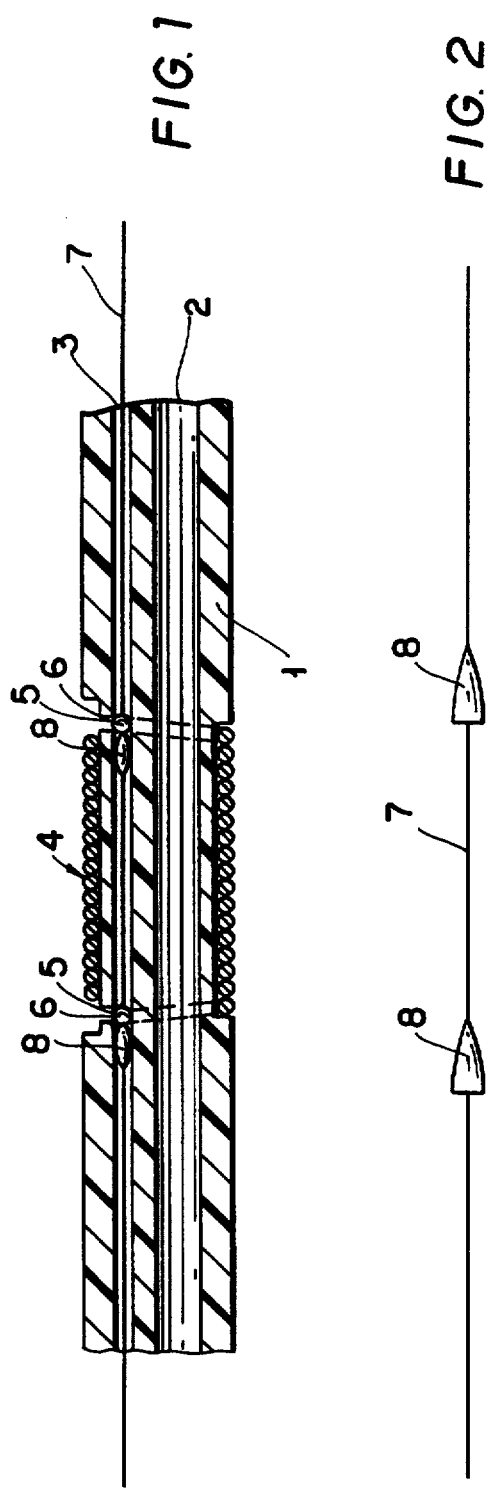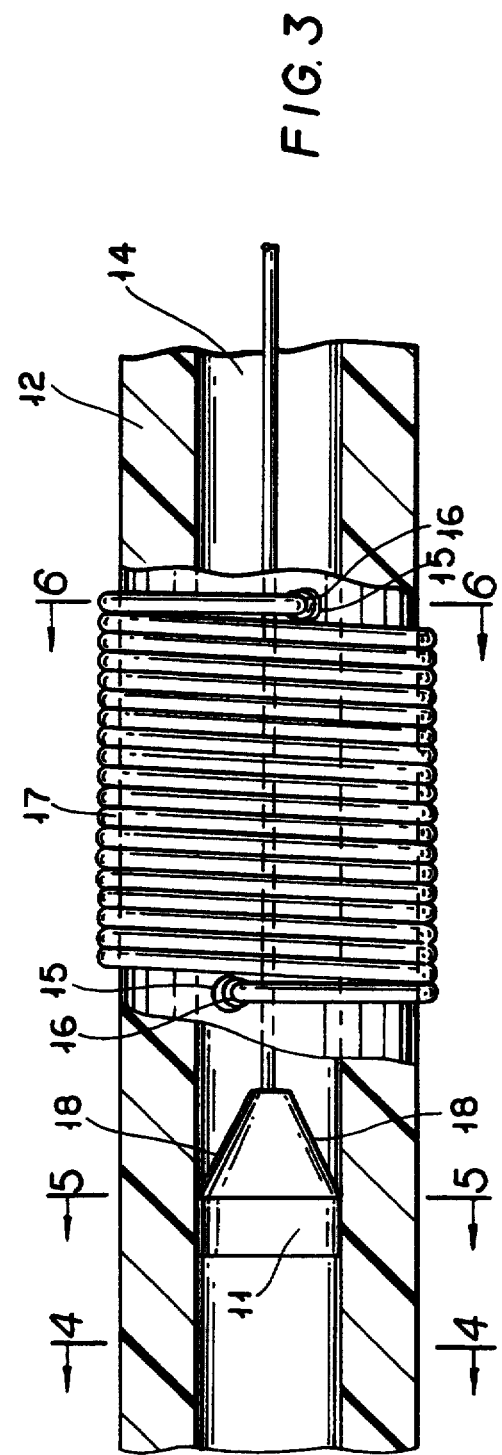

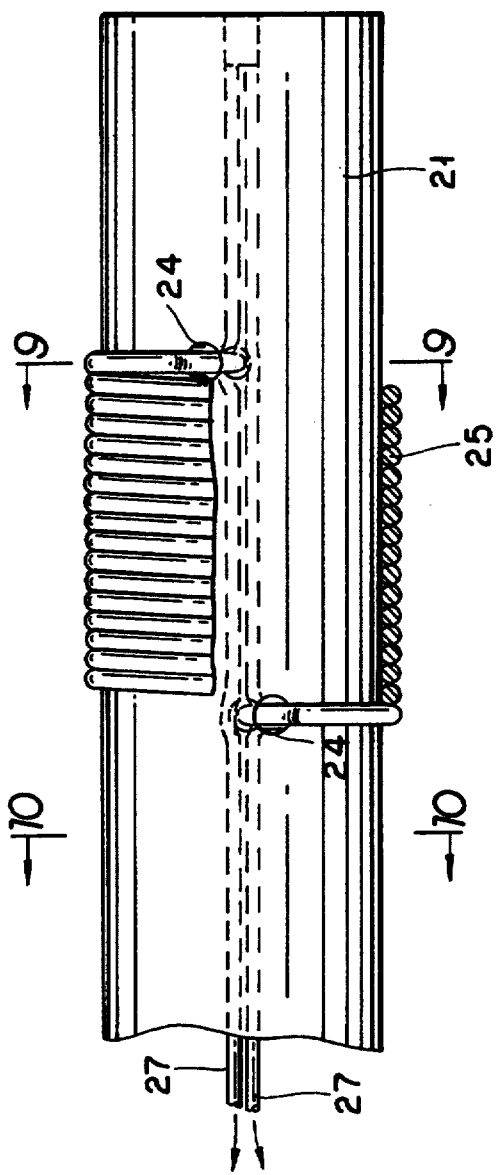
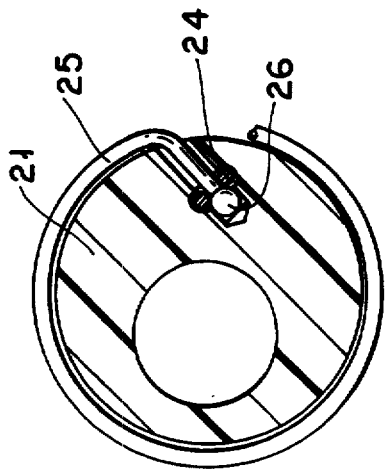
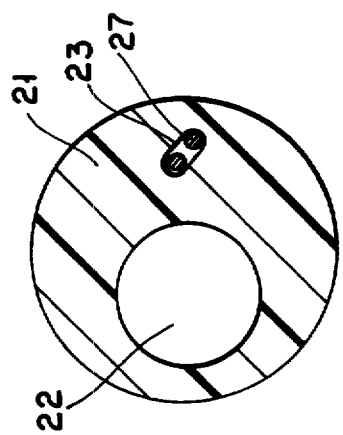

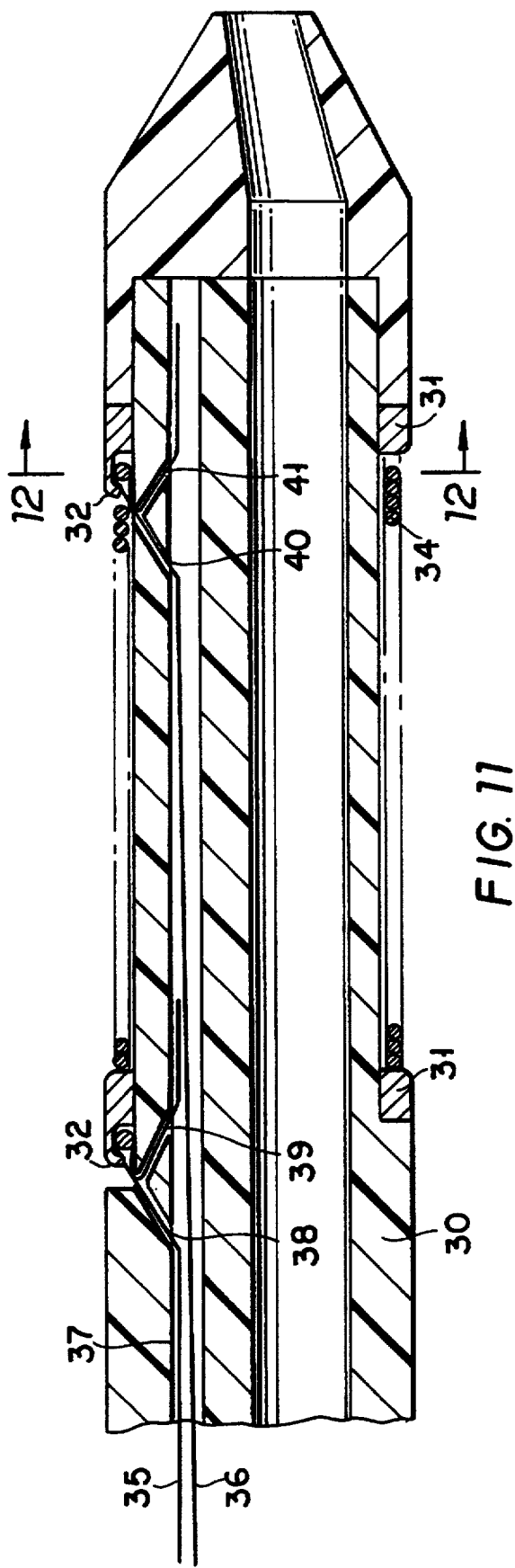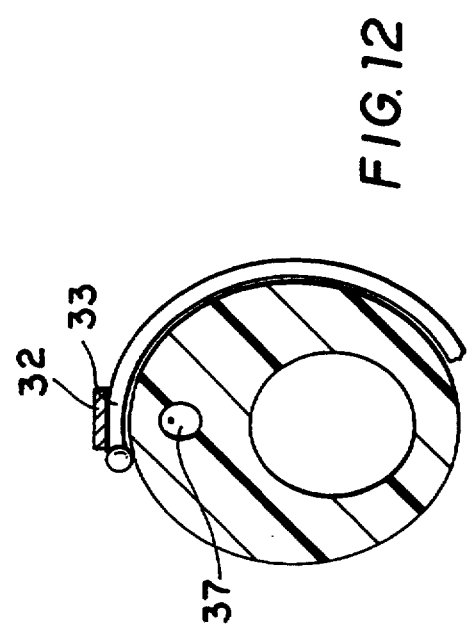

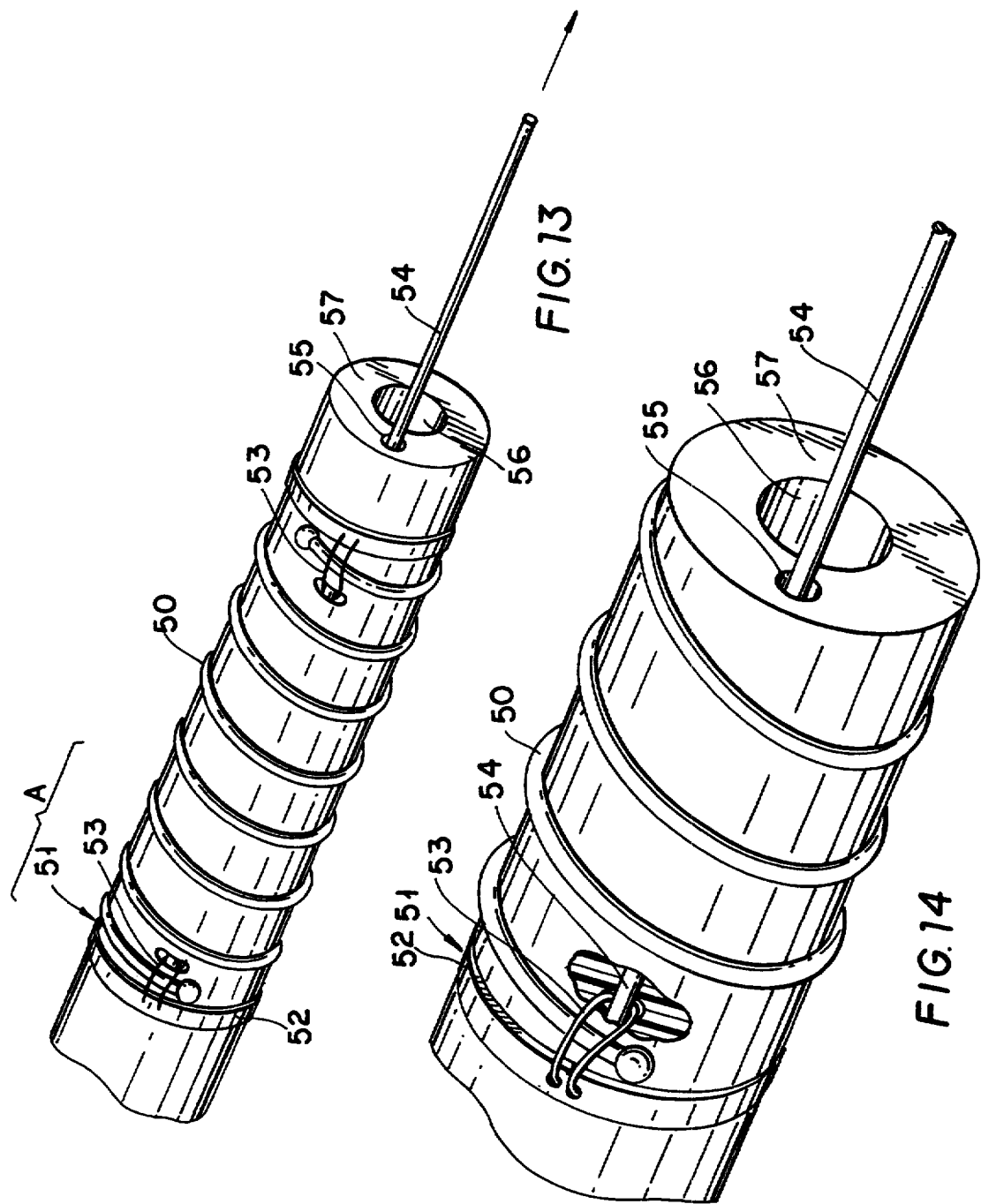

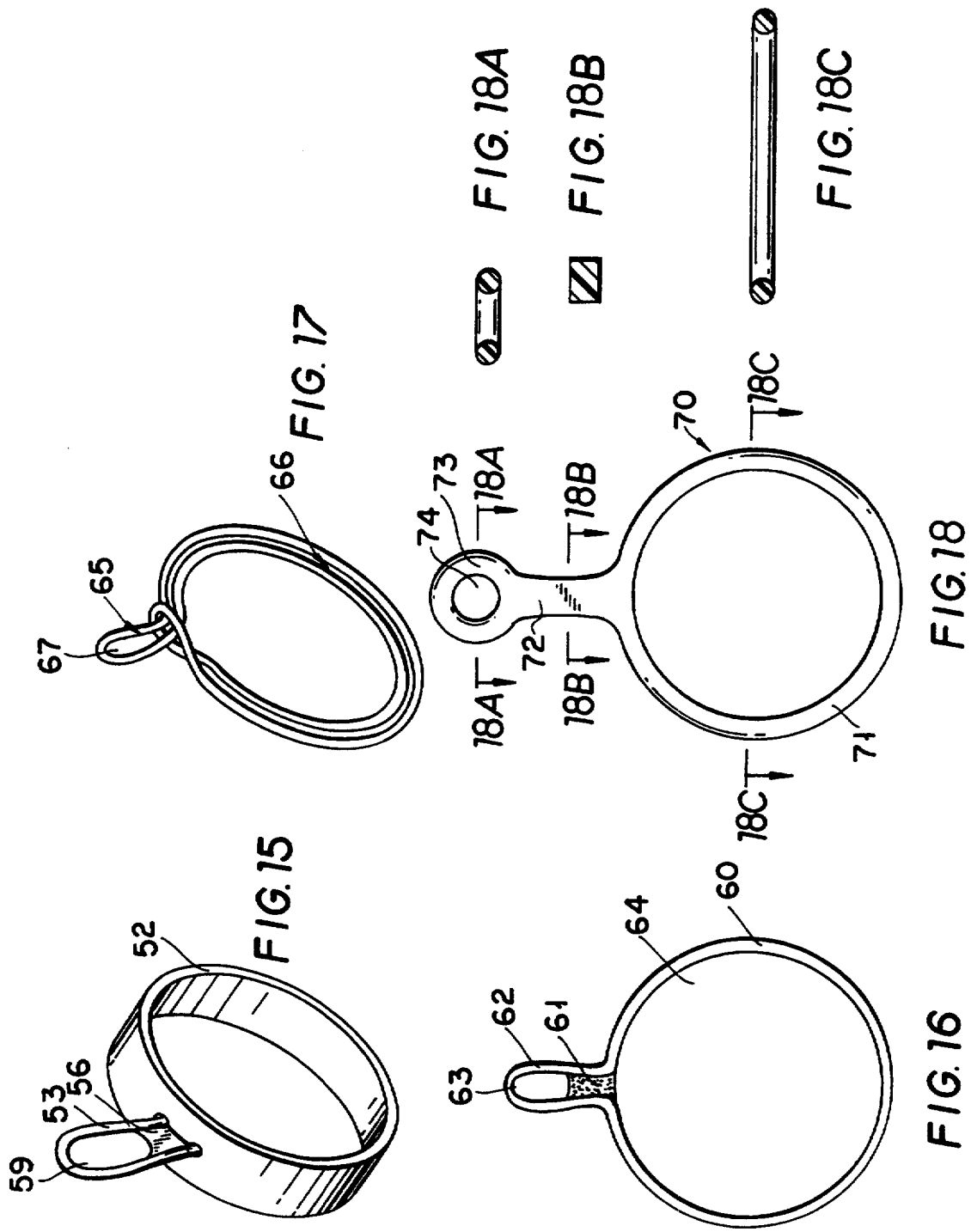

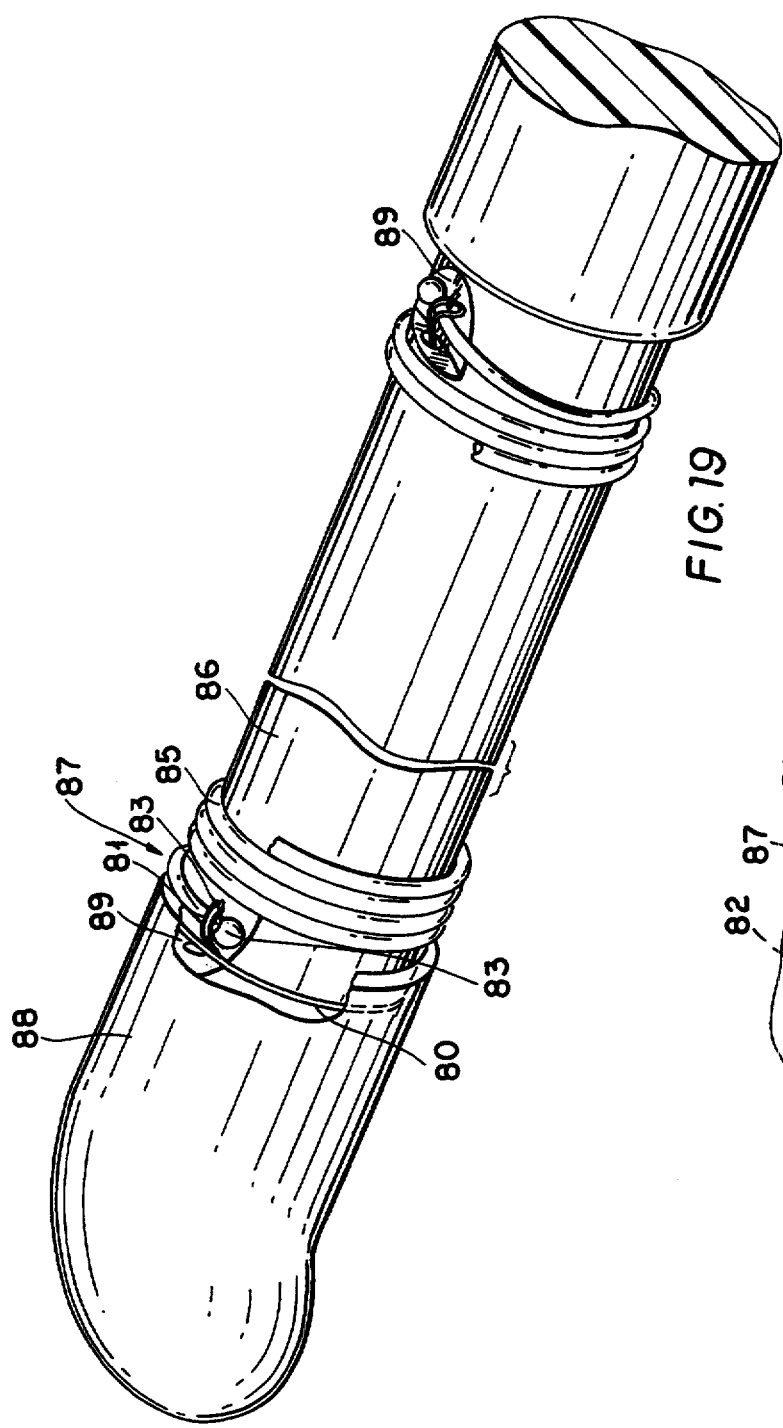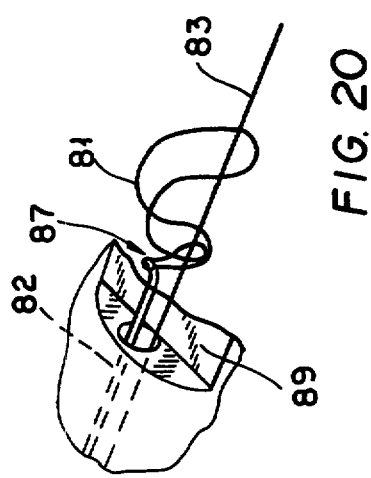

STENT DELIVERY SYSTEMS

CROSS-REFERENCE TO RELATED APPLICATIONS

This application is a continuation-in-part of co-pending U.S. patent application Ser. No. 07/805,737, filed Dec. 11, 1991, now abandoned, which in turn is a continuation-in-part of co-pending U.S. patent application Ser. No. 07/781,174, filed Oct. 31, 1991, now abandoned, which is based upon co-pending PCT Patent Application No. PCT/US91/02716, filed Apr. 19, 1991.

FIELD OF THE INVENTION

This invention is directed to devices for the treatment of constricted ducts in human bodies. More particularly, this invention is directed to intravascular, urethral, ureteral, bronchial, oesophageal, and biliary stents and systems for inserting or implanting them.

BACKGROUND OF THE INVENTION

Urethral strictures can be congenital or acquired. Acquired urethral stricture is common in men but rare in women. Most acquired strictures are due to infection or trauma. Apart from infections caused by venereal diseases, infection from long term use of urethral catheters and the use of large caliber instruments inserted for medical uses into the urethra causes trauma to the urethra. External trauma, e.g., pelvic bone fractures or saddle injuries, can also cause urethral strictures. These narrowings restrict the urine flow. In chronic cases the bladder muscle becomes hypertrophic, and later an increase in the residual urine may develop in the bladder. Prolonged obstruction may cause incompetence of the outflow control mechanism resulting in incontinence or high pressures in the bladder resulting in kidney damage and renal failure. Residual urine may be a predisposing factor for urinary infections which include prostatic infections, urethral abscess and also bladder stones.

Urethral strictures can be managed with palliative treatments such as dilatations of the urethra, which are not curative, because dilatation fractures the scar tissue and temporarily enlarges the lumen. As healing occurs, the scar tissue reforms.

Visually controlled internal urethrotomy is also used in the treatment of urethral strictures. However, in most cases the stricture reoccurs and the procedure has to be repeated.

Plastic surgical repair of the stricture is a meticulous and complicated procedure. However, this procedure has a high recurrence of urethral strictures, and because of the lack of enough experienced surgeons for reconstructive surgery, the majority of cases are managed by non-curative methods.

An intraurethral device designed for urethral strictures made of an expandable tubular mesh is described by E. J. G. Milroy et al., in an article which appeared in the *Journal of Urology* (Vol. 141, May 1989). The device is inserted in a stenotic duct and keeps the lumen open as its inner diameter is larger than the duct lumen. As this device comprises tubular mesh, it becomes incorporated into the urethral wall within 3 to 6 months of insertion, becoming a permanent device and necessitating surgical intervention for its removal.

Bladder outlet obstruction is one of the most commonly encountered disorders in urology. The most frequently occurring anatomical cause of bladder outlet obstruction in males is enlargement of the prostate gland, either by benign hypertrophy or cancer. The prostate is a chestnut-sized gland lying inferior to the bladder and surrounding approximately the first inch of the urethra. As males age, the prostate commonly enlarges—without necessarily being malignant—and tends to gradually narrow or constrict its central opening and thus exert radial, inwardly directed pressure on the prostatic urethra. This condition, known as benign prostatic hyperplasia (BPH), can cause a variety of obstructive symptoms, including urinary hesitancy, straining to void, and decreased size and force of the urinary stream. As the condition gradually worsens, there may be total closure of the urethra and concomitant complete urinary retention. Chronic urinary retention may deteriorate renal function as high intravesical pressure is transmitted to the renal parenchyma.

When intervention is indicated, there has heretofore been no widely accepted alternative to surgery. The preferred surgical procedure is the transurethral resection, wherein a resectoscope is inserted through the external opening of the urethra, and an electrosurgical loop is employed to cut away sections of the prostate gland from within the prostatic urethra. Another surgical intervention is open surgical removal of the gland performed through an abdominal incision. However, as BPH is a typical disease of elderly people, many patients are poor candidates for such major surgery.

Another treatment is balloon dilatation of the prostate. According to that technique, expansion of the prostatic urethra up to a diameter of 3 to 4 cm results in tearing of the prostate commissurae while keeping the prostatic urethra open. The long time efficacy of this treatment has not yet been established. A further treatment is heating the prostatic tissue to a temperature 3° to 5° C. higher than that of the human body, resulting in some histological changes causing some kind of prostatic shrinkage. The efficacy of this treatment is not universally accepted.

Despite the available alternatives to surgery, such as those mentioned above, most high operative risk patients rely on a perpetually worn catheter, as this alternative has proven efficacy for urinary drainage—so far.

A number of devices have been suggested which are said to provide relief from the effects of prostate hypertrophy. European Patent Application No. 027486, which is based upon U.S. patent application Ser. No. 939,754, filed Dec. 9, 1986, describes a balloon expandable stent which is transurethrally inserted and is placed in a stenotic prostatic urethra. The insertion is performed with the aid of a special balloon catheter which is removed after insertion, leaving in the urethra a non-flexible, expanded stent which ensures the maintenance of the open lumen of the prostatic lumen. The lack of flexibility of this stent is a disadvantage due to the high risk of migration of the stent into the bladder. Also, this stent has a mesh design that favors incorporation into the mucosa, thereby becoming a permanent stent, removable only by a major operation.

A full description of the pathology of the male urethra is provided in Campbell's Urology, 5th Edition, 1986, Vol. 1, pages 520–523 and 1217–1234, and Vol. 3, pages 2860–2886 (published by W. B. Saunders Co., Philadelphia, Pa. U.S.A.), which description is incorporated herein by reference.

SUMMARY OF THE INVENTION

The present invention relates to a device intended for use in dealing with constrictions in ducts in the human body to relieve the possible pathological results of such stenoses. One of the frequently occurring such constrictions is that of the male urethra due to urethrostenosis of inflammatory or traumatic origin or benign or malignant enlargement of the prostrate. However, the device of this invention is not intended exclusively for such use but is useful to treat restriction or constriction of other body ducts. Other frequent strictures for which the device according to the invention is useful include those of the ureters, blood vessels, biliary ducts, intestines, airways of the lungs, and fallopian tubes. The attending physician will decide to what extent the new device can be employed in treatment of stenotic conditions of a duct in a human body.

The invention will be described below, using the conditions resulting from prostatic urethral constriction as an example for use of the device. However, as stated above, the invention is not limited to this application.

The invention further relates to means and methods for introducing the device into and depositing it within the urethra (or other duct), to ensure free and unimpeded flow of urine from the bladder to the natural outlet, or of whatever other fluid into or out of the respective bodily conduit.

Treatment by means of the device of this invention can also be applied to all kinds of urethral stricture caused by other causes, such as infections, inflammations, and trauma.

OBJECTS OF THE INVENTION

It is an object of this invention to provide a device for the treatment of constricted ducts in human bodies, such as urethras, ureters, biliary tracts, arteries, and the like.

It is also an object of the invention to provide a suitable material for the coil, being capable of a large expandable ratio and regaining its pre-mounted shape and dimensions, and at the same time having the maximum force of expandability.

It is a further object of the invention to provide a helically wound coil having attachments at the respective ends and an insertion means for inserting said coil into a constricted body duct.

It is a yet further aspect of the invention to provide a helically wound coil comprised of superelastic Nitinol.

These and other objects of the invention will become more apparent in the discussion below.

BRIEF DESCRIPTION OF THE DRAWINGS

FIG. 1 represents a schematic cross-sectional view of an embodiment of a delivery system according to the invention;

FIG. 2 represents lateral view of a release wire useful in the embodiment of FIG. 1;

FIG. 3 represents a pictorial, partly cross-sectional view of another embodiment of the invention which uses the same principles shown in the embodiment of FIGS. 1 and 2;

FIG. 8 represents a pictorial, partly cross-sectional view of further embodiment of the invention;

FIGS. 9 and 10 represent cross-sectional views of the embodiment shown in FIG. 8;

FIG. 11 represents a cross-sectional view of an additional embodiment of the invention;

FIG. 12 represents a lateral cross-sectional view of the embodiment shown in FIG. 11;

FIG. 13 represents an oblique, partly cross-sectional view of an embodiment of the invention;

FIG. 14 represents a close-up of a portion of the embodiment shown in FIG. 13;

FIGS. 15, 16, 17, 18 and 18A–18C are restraining mechanisms useful according to the invention; and FIGS. 19 and 20 represent an additional embodiment of the invention.

DETAILED DESCRIPTION OF THE INVENTION

Figure 6:
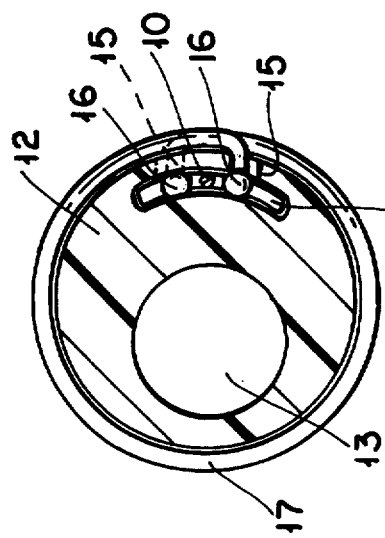
FIGS. 4, 5, and 6 represent cross-sectional views of the embodiment shown in FIG. 3.

This invention is directed to a stent delivery system wherein a stent is releasably held to the distal portion of a catheter and then, once the stent is in a desired position in a constricted area, the stent is released from the catheter. Prior to release, the stent is in a stressed or torqued condition where its profile is reduced, and once the stent is released from the catheter, the stent assumes a non-stressed, non-torqued condition with a larger diameter profile.

These and further features of the invention will become clear from the following detailed description which refers to the drawings. According to FIG. 1, a catheter 1 has central lumen 2, and second or side lumen 3. A stent 4 encompasses catheter 1 near its distal end, and balls 5 at the respective ends of stent 4 extend through openings 6 into side lumen 3. Stent 4 is in a stressed or pre-torqued state, and balls 5 restrain stent 4 from unraveling. Due to the torqued condition of stent 4, its profile is substantially reduced as compared with its non-stressed or non-torqued condition.

Side lumen 3 contains one or two release wires such as release wire 7, which has one or two push members 8, as also shown in FIG. 2. As release wire 7 is pulled proximally, push members 8 cause each ball 5 to move radially towards the catheter external surface to free a respective end of stent 4. One push member 8 could sequentially release each ball 5, or two push members 8, dependent on spacing, could release balls 5 simultaneously or sequentially.

Once the stent 4 is released at both ends and permitted to expand, catheter 1 can be withdrawn proximally.

Push members 8 can be any shape that will be effective to dislocate balls 5. Preferably push members 8 are conical or have a slanted surface that will push balls 5 radially as a release wire 7 is pulled proximally. Also, push members 8 can be separate members attached securely to a release wire 7, such as by gluing, crimping, welding, or soldering, or push members 8 and a release wire 7 could be integral, i.e., formed together.

FIGS. 3 to 7 represent a variation of the embodiment shown in FIG. 1, wherein an angularly profiled, pushing member 10 is at the distal end of release wire 11. Catheter 12 has a central lumen 13, an arc-shaped side lumen 14, and openings 15 for receiving balls 16 of stent 17, which is stressed or torqued. The openings 15 are arranged in an offset pattern so that as release wire 11 is pulled distally, the balls are contacted in turn by sloped surfaces 18 of pushing element 10. The respective contact causes each ball 16 to be released from its respective opening 15, whereby the respective ends of the stent 17 "unwind" and the diameter of stent 17 increases.

Pushing member 10 is affixed or attached securely to the distal end or distal portion of release wire 11. Such attachment or fixation can be by suitable means, for example, gluing, crimping, soldering, or welding. Also, pushing member 10 could be formed integral with release wire 11.

Figure 5:
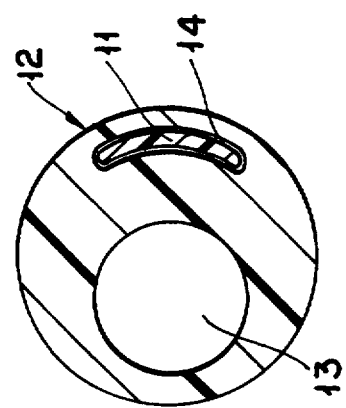
Figure 4:
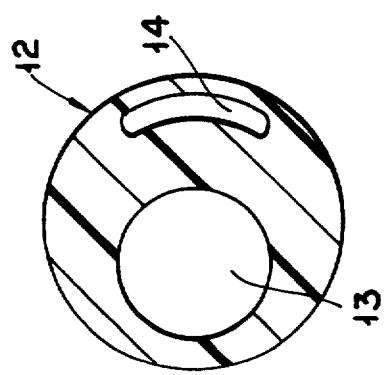
Figure 7:
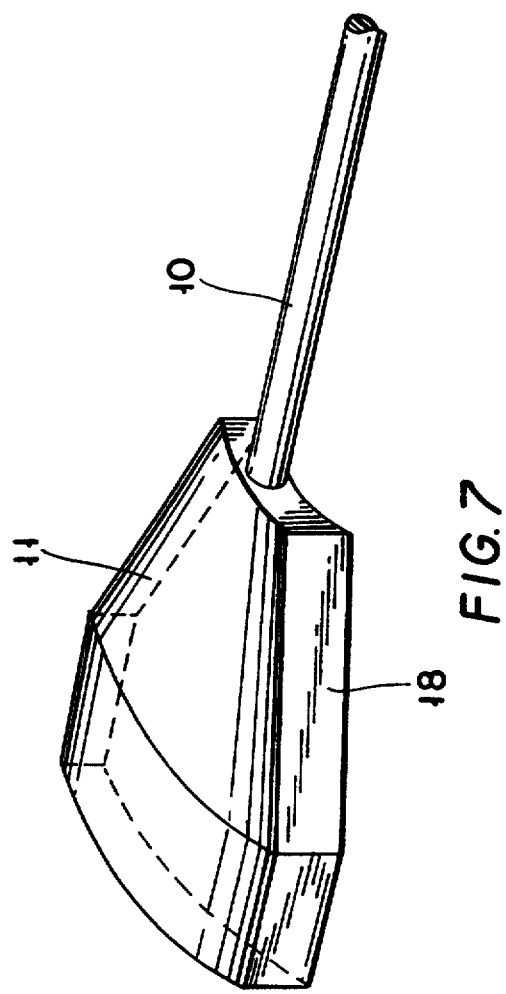
FIG. 7 represents an oblique view of a pushing/pulling element for the embodiment shown in FIG. 3.

FIGS. 4, 5, and 6 depict the manner in which pushing element 10 is positioned within side lumen 14.

The embodiment shown in FIGS. 8, 9, and 10 represents a catheter 21 having central lumen 22 and second or side lumen 23. Side lumen 23 is in communication with openings 24, which are shown with dotted lines.

Stressed or torqued stent 25 has balls 26 at its respective ends. Each ball 26 is held between release wires 27, which extend to the proximal end of catheter 21.

Side lumen 23 is sufficiently small that release wires 27 are pressed together and in turn restrain balls 26. However, as one or both of release wires 27 are moved proximally by the operator, each ball 26 is in turn released, allowing the respective end of the stent 25 to be released from the catheter 21.

The embodiment shown in FIGS. 11 and 12 comprises a catheter 30 having elastic metal rings 31. Each metal ring 31 has a holder 32 to restrain an end portion 33 of a stent 34. Release wires 35, 36 extend through side lumen 37 and channels 38, 39, 40, and 41 to encompass distal portions 33. When release wired 35, 36 are each moved proximally, stent end portions 33 are released from holders 32.

It is within the scope of the invention that release wires 35, 36 may be replaced by a single release wire. Also, each of release wires 35, 36 could be in a separate side lumen.

In the embodiment of the invention set forth in FIG. 13, the respective distal and proximal ends of a stent 50 are restrained by a restraining means 51 comprising a band 52 and a fixation member 53. Two ends of fixation member 53 are attached to band 52 and the loop side of fixation member 53 passes over the external lateral surface of the stent 50 and is held within second or side lumen 55 by one or more fixation wires 54. Fixation wire 54 is contained within side lumen 55 which is adjacent to one or more main or central lumens 56 of catheter 57. It is within the scope of the invention that a fixation wire 54 may extend through each of two separate side lumens 55 and/or that three fixation wires 55 may extend through two or three separate side lumens 55, where either one fixation wire would extend through each of three separate side lumens 55 or one fixation wire 54 would extend through one side lumen 55 and two fixation wires 54 would extend through a second, side lumen 55.

Preferably fixation member 53 has a weld, solder, or glue member 56 that decreases the size of the opening within fixation member 53, to ensure that the ball 58 at the end of the stent 50 does not become caught in said opening after stent deployment within the body duct.

The restraining mechanism is shown somewhat more clearly in FIG. 14, which represents a close-up of the portion of FIG. 13 identified as section A.

The restraining mechanism 51 is shown somewhat more clearly in FIG. 15. It would be appreciated by one skilled in the art that loop 53 and band 52 could have various functional equivalents, such as, for example, the embodiments shown in FIGS. 16 and 17. In FIG. 16, a continuous closed piece of metal or polymer wire 60 has a weld 61 that defines loop 62 with opening 63 and effective band member 64. Such a material could be comprised of any physiological acceptable or medically acceptable wire of appropriate flexibility, preferably having a diameter of from 0.05 to 0.4 mm.

With regard to the restraining mechanisms shown in FIGS. 15, 16, and 17, it should be appreciated that in an alternative arrangement the loops 53, 62, or 65 could be twisted to define opening 59, 63, or 67, whereby the twisted portion of loop 53, 62, or 65 would be held by suitable means, such as glue, solder, or a weld. Preferably the twisted portion will be held by a glue such that the loop will remain flexible.

In the band or restraining mechanism 51 shown in FIG. 17, a flexible strand of material has been arranged to define loop 65 and band 66. Such a strand could be comprised of any suitable flexible material such as silk, string, an appropriate polymer, or even small diameter braided wire.

An additional embodiment of a restraining mechanism is shown in FIG. 18, wherein the restraining mechanism 70 comprises band 71, connector 72, and loop 73. Loop 73 defines opening 74. Preferably, band 71 and loop 73 have circular or oval cross-sections and connector 72 has a rectangular cross-section. Restraining mechanism 70 is preferably comprised of a suitable polymer or co-polymer selected from the group consisting of nylon, polyethylene, polypropylene, polyvinylchloride, and copolymers of one or more of these polymers. It is within the scope of the invention that restraining mechanism 70 could be comprised of two separate polymers; for example, band 71 would be made of a rigid polyethylene/polypropylene co-polymer whereas connector 72 and loop 73 would be made from a more flexible polymer such as polyethylene.

An additional embodiment of the invention is shown in FIGS. 19 and 20. A restraining mechanism 87 comprises restraining band 80 having a loop means 81 connected by connector 82. Loop means 81 is arranged relative to restraining wire 83 such that the distal end 84 of stent 85 will be held against catheter 86. Restraining mechanism 87 may be covered partly or wholly by a sheath 88. Also, a portion of restraining mechanism 87 may be fitted in a notch or groove 87.

The stent delivery systems described herein are intended to be useful for the stents shown as well as other expandable stents. A preferred stent, such as that shown here, is described in co-pending U.S. patent application Ser. No. 07/781,174, filed Oct. 31, 1991, incorporated herein by reference.

More specifically, the preferred stent comprises a spatial spiral (helix) wound of wire of a material tolerated by the human body and which, furthermore, is not corroded or otherwise attacked by body liquids. Such a material, also known as a physiologically or medically acceptable material, could be one or more of several materials known for this purpose. Especially useful here are metals such as stainless steel, gold-plated medical grade stainless steel, stainless steel coated with silicone, bicarbon, or polytetrafluoroethylene, such as TEFLON ®, tantalum, titanium, superelastic alloy such as nickel-titanium (Ni-Ti) alloys (commercially available as Nitinol or Tinel), or bioabsorbable material. The wire typically has a diameter of from about 0.1 to 1.0 mm, preferably from about 0.15 to 0.60 mm. Also, a strip of ellipsoidal, rectangular, rectangular with step, or S-shape wire is suitable for stent production.

It is important that the winding of the stent be sufficiently tight that the outer surface of the device is substantially continuous, thus preventing "leaking through" of the inner lining of a vessel or duct. However, in cases in which incorporation of the stent into the wall of a duct is preferred, space of about 0.1 to 2.0 mm will be left between the loops of the coil.

The preferred stent useful herein has thickened regions at the distal and proximal ends of the stent. In the text above reference is made to "ball 5"; however, each ball 5 can be spherical or non-spherical, so long as the "ball" functions as described. For example, in the embodiment shown in FIGS. 13 and 14, the "ball 5" could merely be a non-spherical thickened area, such as an egg, cone, or tear-drop shape, or a functionally equivalent loop, hole, or hook, that would cooperate with loop 53 to restrain an end of the stent.

The outer diameter and length of the device will vary according to the intended use. For prostatic or urinary use, the outer diameter of the wound device will typically be from about 10 to 40 French (from about 3.3 to 13.3 mm), and the length of the device can vary from about 2 to 15 cm, preferably from about 4 to 12 cm. It is also within the scope of the invention that the device may comprise two spirals connected by a wire, the spirals and wire preferably being a continuous wire.

A special property of nickel-titanium alloy (Nitinol) is used for the production of the stent. Nickel-titanium alloy can have superelasticity at a given temperature, for example, at body temperature (37° C.). The term "superelasticity" is used to describe the property of certain alloys to return to their original shape upon unloading after substantial deformation. Superelastic alloys can be strained up to ten times more than ordinary spring materials without being plastically deformed. Such superelasticity would enable one to compress the stent to a very small diameter over the delivery catheter. Elasticity is also available in Nitinol as a shape memory material, but then the radial force is lower and a temperature difference has to be applied during insertion of the stent, a procedure which makes the insertion more complicated, painful, and risky.

Another application of the invention is to open the prostatic urethral lumen to a very large diameter (30 to 40 mm diameter), resulting in divulsion of the prostatic commissure and shrinkage of prostatic tissue. This method results in opening of the prostatic lumen and freeing of the patient from the obstruction caused by the pressure of the gland. This method has an advantage over the balloon dilatation of the prostate in that it opens the prostatic urethra slowly over a long period (up to a few days) and in that the constant pressure on prostatic tissue causes pressure atrophy. This atrophy makes prostatic volume smaller—and by doing so allows good urinary flow through the prostatic urethra. (Balloon dilatation results only in divulsion of prostatic commissures.) This method cannot be applied in the balloon dilatation of the prostate because in this short time procedure there is only tearing of prostatic commissures but not atrophy and lessening of prostatic cells, such as occurs with slow prostatic dilatation.

In prostatic strictures or in urethral strictures near the external sphincter there is a high risk of stent migration in the first one to the bladder and in the second one towards the penile meatus. To overcome this another two parts are added to the stent, namely, another open wire and another short closed loop (1-2 cm). The straight wire is for holding the stent in the external sphincter area which is the fixed strongest part of the urethra. A system like this exists in Prostacath, a prostatic stent, and also in urethral prostheses manufactured in France.

In both of these stents the wire is a straight wire which makes it less flexible and doesn't allow easy movements of both spirals, one at an angle to the other. This situation applies more constant pressure on the bulbar and prostatic urethra and may cause stent penetration into the urethral lumen as well as urethral perforation/fistula—cases which have been reported in literature.

Here, a half to one turn straight wire curve in the circumference of the stent, is used between the two coils. This allows more flexibility of the wire and more free movement of both the distal and proximal spring portions of the stent. Also it doesn't disturb passing instruments through the stent lumen as this loop wire goes in the "periphery" of the stent lumen.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. Apparatus for implanting a flexible, generally cylindrical, expandable stent, comprising:
   a catheter having distal and proximal ends, said catheter defining a central lumen and a second lumen extending therethrough and having two longitudinally displaced openings extending from the second lumen radially to the surface of the catheter,
   a flexible, expandable stent having discrete proximal and distal ends, said stent being positioned circumferentially around said catheter and said discrete ends extending into said openings to hold said stent in position, and
   at least one release wire positioned in and extending through the second lumen, said release wire or wires fixedly containing at least one conically shaped pushing member capable of causing a discrete end of said stent to move radially as the release wire or wires are moved proximally.

2. The apparatus of claim 1, wherein the discrete ends of the stent have balls.

3. The apparatus of claim 1, wherein there is only one release wire.

4. The apparatus of claim 3, wherein the release wire contains two pushing members.

5. The apparatus of claim 4, wherein the pushing members are spaced apart at a distance equal to the distance between said openings.

6. The apparatus of claim 4, wherein the distance between the pushing members is different from the distance between said openings.

7. The apparatus of claim 1, wherein the stent is comprised of a superelastic alloy.

8. The apparatus of claim 7, wherein the superelastic alloy is a nickel-titanium alloy (Nitinol).

9. The apparatus of claim 8, wherein the alloy is superelastic, having high elasticity such that the stent assumes its original, unwound shape after stent diameter reduction.

10. Apparatus for implanting a flexible, generally cylindrical, expandable stent, comprising:
    a catheter having distal and proximal ends, said catheter defining a central lumen and from one to three secondary lumens extending therethrough and having two or three longitudinally displaced openings extending from the secondary lumen or lumens radially to the surface of the catheter, a flexible, expandable stent having discrete proximal and distal ends, said stent being positioned circumferentially around said catheter, one or more release wires positioned in and extending through the second lumen or lumens, and two or three restraining means positioned proximal and distal to the stent, respectively, each of said restraining means comprising a loop member having two ends, one of which ends is positioned on the outer surface of the catheter and the other of which ends has an opening therein, such that said loop member is positioned across the external surface of said stent end and extends into a respective radial opening to intersect a release wire, such that when said release wire or wires are pulled proximally the loop members disengage the ends of the stent and the stent uncoils.

11. The apparatus of claim 10, wherein the loop members are flexible or rigid.

12. The apparatus of claim 10, wherein a loop member is positioned around a release wire on each side of said stent end.

13. The apparatus of claim 10, wherein a loop member is positioned around a release wire on one side of said stent end.

14. The apparatus of claim 10, wherein the stent is comprised of superelastic alloy.

15. The apparatus of claim 10, wherein there is only one release wire.

16. The apparatus of claim 10, wherein there are two release wires, the wires engaging loop members at the proximal and distal ends of the stent, respectively.

17. The apparatus of claim 16, wherein each release wire extends through a separate secondary lumen.

18. The apparatus of claim 10, wherein there are only two restraining means, which are positioned at the proximal and distal ends of the stent, respectively.

19. The apparatus of claim 10, wherein there are three restraining means, which are positioned at the proximal end, the middle, and the distal end of the stent, respectively.

20. The apparatus of claim 10, wherein the catheter has a section of reduced external diameter substantially coextensive with the stent.

21. Apparatus for implanting a flexible generally cylindrical, expandable stent, comprising:

a catheter having distal and proximal ends, said catheter defining a central lumen and from one to three secondary lumens extending therethrough and having two or more longitudinally displaced openings extending from the secondary lumen or lumens to the surface of the catheter, a flexible expandable stent having discrete proximal and distal ends, said stent being positioned circumferentially around said catheter, at least one release wire positioned in and extending through the secondary lumen or lumens, and two or three restraining means, two of which are positioned at respective ends of the stent and each having a restraining member extending over a respective end of the stent, the release wire or wires extending through at least one of said openings to hold one or both ends of the stent and thus to hold the stent in position, such that when the release wire or wires are pulled proximally, one or both ends of the stent are released from the restraining members to permit the stent to expand.

22. The apparatus of claim 21, wherein each restraining member is flexible or rigid.

23. The apparatus of claim 21, wherein a restraining member is positioned around a release wire on each side of said stent end.

24. The apparatus of claim 21, wherein a restraining member is positioned around a release wire on one side of said stent end.

25. The apparatus of claim 21, wherein the stent is comprised of superelastic alloy.

26. The apparatus of claim 21, wherein there is only one release wire.

27. The apparatus of claim 21, wherein there are two release wires, the wires engaging loop members at the proximal and distal ends of the stent, respectively.

28. The apparatus of claim 27, wherein each release wire extends through a separate secondary lumen.

29. The apparatus of claim 21, wherein there are only two restraining means, which are positioned at the proximal and distal ends of the stent, respectively.

30. The apparatus of claim 21, wherein there are three restraining means, which are positioned at the proximal end, the middle, and the distal end of the stent, respectively.

31. The apparatus of claim 21, wherein the catheter has a section of reduced external diameter substantially coextensive with said stent.

32. Apparatus for implanting a flexible, generally cylindrical, expandable stent, comprising:

a catheter having distal and proximal ends, said catheter defining a central lumen and a second lumen extending therethrough and having two longitudinally displaced openings extending from the second lumen radially to the surface of the catheter, a flexible, expandable stent having discrete proximal and distal ends, said stent being positioned circumferentially around said catheter and said discrete ends extending into said openings to hold said stent in position, and a release wire positioned in and extending through the second lumen, said release wire fixedly containing a pushing member capable of causing a discrete end of said stent to move radially as the release wire is moved proximally, wherein the second lumen is substantially arcuate shaped, the pushing member has a cross-section of similar shape, the proximal portion of the pushing member has two oppositely positioned sloping faces, and the openings in the catheter are offset such that one sloping face intersects the plane of one opening and the other sloping face intersects the plane of the other opening, as the release wire is pulled distally.

33. The apparatus of claim 32, wherein the discrete ends of the stent have balls.

34. The apparatus of claim 32, wherein the stent is comprised of a superelastic alloy.

* * * * *